(12) United States Patent
Xu et al.

(10) Patent No.: US 11,165,097 B2
(45) Date of Patent: Nov. 2, 2021

(54) ELECTROLYTE, ELECTROCHEMICAL DEVICE AND ELECTRONIC DEVICE CONTAINING THE SAME

(71) Applicant: NINGDE AMPEREX TECHNOLOGY LIMITED, Ningde (CN)

(72) Inventors: Chunrui Xu, Ningde (CN); Wenqiang Li, Ningde (CN); Chao Tang, Ningde (CN); Shuirong Zhang, Ningde (CN)

(73) Assignee: NINGDE AMPEREX TECHNOLOGY LIMITED, Ningde (CN)

( * ) Notice: Subject to any disclaimer, the term of this patent is extended or adjusted under 35 U.S.C. 154(b) by 202 days.

(21) Appl. No.: 16/454,904

(22) Filed: Jun. 27, 2019

(65) Prior Publication Data
US 2020/0243905 A1 Jul. 30, 2020

(30) Foreign Application Priority Data
Jan. 25, 2019 (CN) .......................... 201910071427.3

(51) Int. Cl.
| | | |
|---|---|---|
| H01M 10/0564 | (2010.01) | |
| H01M 10/0525 | (2010.01) | |
| C01B 25/30 | (2006.01) | |
| C07D 327/02 | (2006.01) | |
| C07D 327/10 | (2006.01) | |
| C07F 7/18 | (2006.01) | |
| H01M 4/62 | (2006.01) | |

(52) U.S. Cl.
CPC ... *H01M 10/0564* (2013.01); *H01M 10/0525* (2013.01); *C01B 25/30* (2013.01); *C07D 327/02* (2013.01); *C07D 327/10* (2013.01); *C07F 7/1896* (2013.01); *H01M 4/623* (2013.01); *H01M 2300/0034* (2013.01)

(58) Field of Classification Search
CPC ........... H01M 10/052; H01M 10/0525; H01M 10/0564; H01M 10/0567; H01M 2300/0025; H01M 2300/0034; H01M 4/623
See application file for complete search history.

(56) References Cited

U.S. PATENT DOCUMENTS

| | | | |
|---|---|---|---|
| 2007/0054179 A1 | 3/2007 | Kusachi et al. | |
| 2019/0348713 A1* | 11/2019 | Yu ..................... | H01M 10/0567 |

FOREIGN PATENT DOCUMENTS

| | | | |
|---|---|---|---|
| CN | 100395905 C | 6/2008 | |
| CN | 101271987 A | 9/2008 | |
| CN | 102544586 A | 7/2012 | |
| CN | 103715458 A | 4/2014 | |
| CN | 103825049 A | 5/2014 | |
| CN | 104025353 A | 9/2014 | |
| CN | 105009347 A | 10/2015 | |
| CN | 105098238 A | 11/2015 | |
| CN | 105489936 A | 4/2016 | |
| CN | 105514487 A | 4/2016 | |
| CN | 105895957 A | 8/2016 | |
| CN | 106025359 A | 10/2016 | |
| CN | 109256592 A | 1/2019 | |
| CN | 109904521 A | 6/2019 | |
| JP | 2002280063 A | * | 9/2002 |
| JP | 2002280063 A | | 9/2002 |
| JP | 2005339952 A | | 12/2005 |
| JP | 2005339952 A | * | 12/2005 |
| JP | 3961597 B2 | | 8/2007 |
| JP | 2009252645 A | | 10/2009 |

OTHER PUBLICATIONS

H. Rong, M. Xu, Y. Zhu, B. Xie, H. Lin, Y. Liao, L. Xing, W. Li. A novel imidazole-based electrolyte additive for improved electrochemical performance of high voltage nickel-rich cathode coupled with graphite anode lithium ion battery, Journal of Power Sources 332 (2016) 312-321.*

H. Rong, M. Xu, B. Xie, H. Lin, Y. Zhu, X. Zheng, W. Huang, Y. Liao, L. Xing, W. Li. A novel imidazole-based electrolyte additive for improved electrochemical performance at elevated temperature of high-voltage LiNi0.5Mn1.5O4 cathodes, Journal of Power Sources 329 (2016) 586-593.*

Chinese First Office Action dated Apr. 28, 2020 in counterpart Chinese application CN 201910071427.3, 11 pages.

Rong et al., "A novel imidazole-based electrolyte additive for improved electrochemical performance of high voltage nickel-rich cathode coupled with graphite anode lithium ion battery," Journal of Power Sources 332 (2016), pp. 312-321.

Chinese Second Office Action dated Nov. 27, 2020 in counterpart Chinese application CN 201910071427.3, 11 pages in Chinese.

Chinese Office Action dated Apr. 6, 2021, in connection with corresponding CN Application No. 201910071427.3 (17 pp., including machine-generated English translation).

* cited by examiner

*Primary Examiner* — Carlos Barcena
(74) *Attorney, Agent, or Firm* — Maier & Maier, PLLC

(57) ABSTRACT

The present application relates to an electrolyte, an electrochemical device and an electronic device comprising the same. The electrolyte of the present application includes a cyclic N-containing sulfonyl-compound and at least one of vinylene carbonate, fluoroethylene carbonate, lithium tetrafluoroborate, lithium difluoro(oxalato)borate or lithium difluorophosphate. The electrolyte of the present application may further include a sulfur-oxygen double bond containing compound and a silicon-containing carbonate. Compared with the prior art, using the electrolyte provided by the present application can effectively improve the high-temperature storage, cycle performance and overcharge performance of an electrochemical device, such as a lithium-ion battery.

13 Claims, No Drawings

ELECTROLYTE, ELECTROCHEMICAL DEVICE AND ELECTRONIC DEVICE CONTAINING THE SAME

CROSS REFERENCE TO RELATED APPLICATIONS

The present application claims the benefit of priority from the China Patent Application No. 201910071427.3, filed on 25 Jan. 2019, the disclosure of which is hereby incorporated by reference in its entirety.

BACKGROUND

1. Technical Field

The present application relates to an electrolyte. More specifically, the present application relates to an electrolyte that can improve the high-temperature storage and cycle performance of an electrochemical device (such as a lithium-ion battery). The present application also relates to an electrochemical device and an electronic device containing the electrolyte according to the present application.

2. Description of the Related Art

At present, lithium-ion batteries have been widely used in fields such as electric vehicles, consumer electronics and energy storage devices, and have gradually become the conventional battery in the above fields due to their advantages, such as high energy density and no memory effect, etc. Increasing voltage is one of the options for increasing energy density. However, along with higher energy density there comes a serious challenge to high-temperature storage and cycle performance. Therefore, how to further improve the high-temperature storage and cycle performance of lithium-ion batteries has become a top research focus for all lithium-ion battery manufacturers and related fields.

Using electrolyte additives to improve high-temperature storage and cycle performance has been adopted by many research and development workers. However, most additives improve high-temperature storage by forming a film on the anode, but this usually tends to result in a too high viscosity or results in the film having a too large impedance, which affects the cycle performance and high-temperature storage performance of the battery. In order to meet market demand, there is still a need to develop electrolyte additives capable of effectively improving the high-temperature storage performance and the cycle performance at the same time.

SUMMARY

The present application relates to an electrolyte, comprising a cyclic N-containing sulfonyl-compound and at least one of vinylene carbonate (VC), fluoroethylene carbonate (FEC), lithium tetrafluoroborate (LiBF$_4$), lithium difluoro(oxalato)borate (LiDFOB) or lithium difluorophosphate (LiPO$_2$F$_2$).

According to some embodiments of the present application, the cyclic N-containing sulfonyl-compound is selected from the following compounds of Formula I,

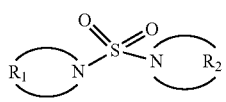

Formula I wherein R$_1$ and R$_2$ are each independently C$_3$-C$_5$ hydrocarbyl or C$_1$-C$_5$ hydrocarbyl containing 1-5 heteroatoms selected from at least one of N, O, P or S.

According to some embodiments of the present application, the cyclic N-containing sulfonyl-compound includes at least one of the following compounds of Formula I-1 to Formula I-7:

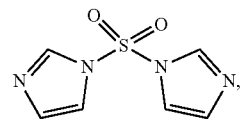

(I-1)

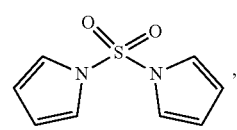

(I-2)

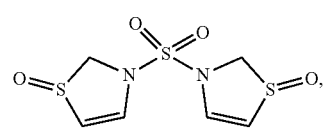

(I-3)

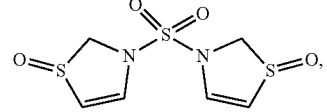

(I-4)

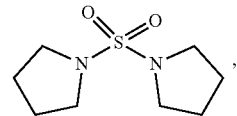

(I-5)

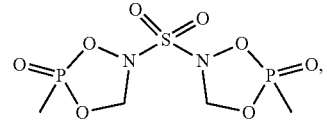

(I-6)

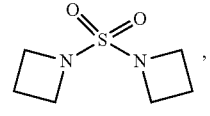

(I-7)

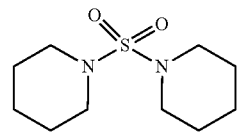

According to some embodiments of the present application, the electrolyte further includes a sulfur-oxygen double bond containing compound, wherein the sulfur-oxygen double bond containing compound includes at least one of the following compounds of Formula II-A, II-B or II-C:

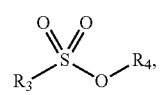

(II-A)

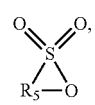

(II-B)

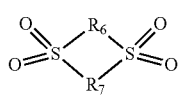

(II-C)

wherein, $R_3$ and $R_4$ are each independently selected from substituted or unsubstituted $C_{1-5}$ alkyl, substituted or unsubstituted $C_{2-10}$ alkenyl, substituted or unsubstituted $C_{6-10}$ aryl or substituted or unsubstituted $C_{1-6}$ heterocyclic group; wherein, when substituted, they are substituted with one or more substituents selected from halogen, cyano, carboxy or sulfate group;

$R_5$ is selected from substituted or unsubstituted $C_{1-4}$ alkylidene, substituted or unsubstituted $C_{2-4}$ alkenylene, or substituted or unsubstituted $C_{1-6}$ chain alkane containing 1-5 heteroatoms selected from N, O, P and S, wherein, when substituted, they are substituted with one or more substituents selected from halogen, $C_{1-3}$ alkyl or $C_{2-4}$ alkenyl;

$R_6$ and $R_7$ are each independently selected from substituted or unsubstituted $C_{1-4}$ alkylidene, substituted or unsubstituted $C_{2-4}$ alkenylene, or substituted or unsubstituted $C_{1-6}$ chain alkane containing $C_{1-5}$ heteroatoms selected from N, O, P and S, wherein, when substituted, they are substituted with one or more substituents selected from halogen, $C_{1-3}$ alkyl or $C_{2-4}$ alkenyl.

According to some embodiments of the present application, the sulfur-oxygen double bond containing compound includes at least one of the following compounds of Formula II-1 to Formula II-8:

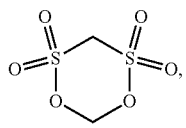

(II-1)

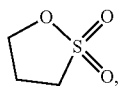

(II-2)

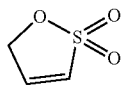

(II-3)

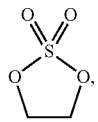

(II-4)

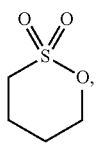

(II-5)

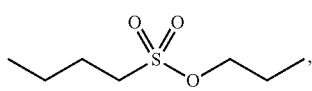

(II-6)

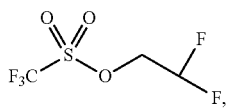

(II-7)

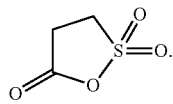

(II-8)

According to some embodiments of the present application, the electrolyte of the present application further includes a silicon-containing carbonate, wherein the silicon-containing carbonate is selected from the following compounds of Formula III or Formula IV:

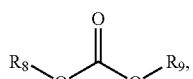

(III)

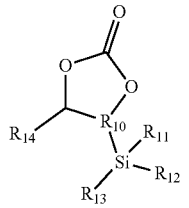

(IV)

wherein, $R_8$ and $R_9$ are each independently selected from $R^a$, —Si—$(R'')_3$ or —R'—Si—$(R'')_3$, and at least one of $R_8$ and $R_9$ contains Si;

$R^a$ and $R''$ are each independently selected from H, $C_{1-12}$ alkyl, $C_{2-12}$ alkenyl, $C_{6-10}$ cyclohydrocarbyl or $C_{6-26}$ aryl; R' is selected from $C_{1-12}$ alkylidene or $C_{2-12}$ alkenylene; $R_8$ and $R_9$ are optionally substituted by halogen;

$R_{10}$ is C—$R^b$, and $R^b$ is selected from H, F, substituted or unsubstituted $C_{1-6}$ alkyl, or substituted or unsubstituted $C_{2-6}$ alkenyl; and $R_{11}$, $R_{12}$, $R_{13}$ and $R_{14}$ are independently selected from substituted or unsubstituted $C_{1-6}$ alkyl, substituted or unsubstituted $C_{1-6}$ alkoxy, substituted or unsubstituted $C_{2-6}$ alkenyl, or substituted or unsubstituted $C_{6-10}$ aromatic ring, wherein the substituent is selected from halogen, $C_1$-$C_6$ alkyl or $C_2$-$C_6$ alkenyl.

According to some embodiments of the present application, the silicon-containing carbonate includes at least one of the following compounds of Formula III-1 to Formula III-5 and compounds of Formula IV-1 to Formula IV-3:

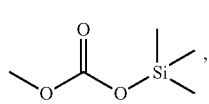

(III-1)

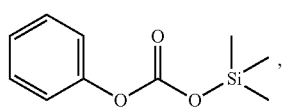

(III-2)

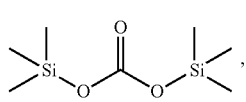

(III-3)

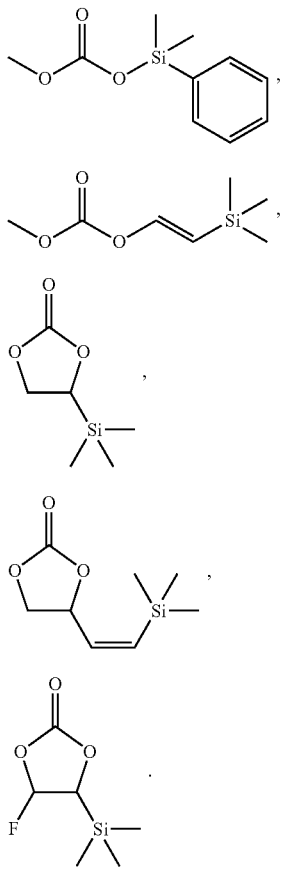

(III-4)
(III-5)
(IV-1)
(IV-2)
(IV-3)

According to some embodiments of the present application, based on the total weight of the electrolyte, the content of the cyclic N-containing sulfonyl-compound is about 0.01 wt % to about 5 wt %, the content of the vinylene carbonate is about 0.001 wt % to about 4 wt %, the content of the fluoroethylene carbonate is about 0.1 wt % to about 10 wt %, the content of the lithium tetrafluoroborate is about 0.001 wt % to about 2 wt %, the content of the lithium difluoro (oxalato)borate is about 0.001 wt % to about 2 wt %, and the content of the lithium difluorophosphate is about 0.001 wt % to about 2 wt %.

According to some embodiments of the present application, based on the total weight of the electrolyte, the content of the sulfur-oxygen double bond containing compound is about 0.01 wt % to about 10 wt %.

According to some embodiments of the present application, based on the total weight of the electrolyte, the content of the silicon-containing carbonate is about 0.1 wt % to about 20 wt %.

The present application further relates to an electrochemical device including any of the above mentioned electrolytes.

The present application further relates to an electronic device including the electrochemical device according to the present application.

Compared with the prior art, using the electrolyte provided by the present application can effectively improve the high-temperature storage performance, cycle performance and overcharge performance of an electrochemical device such as a lithium-ion battery.

DETAILED DESCRIPTION

The embodiments of the present application will be described in detail below. The embodiments of the present application should not be construed as a limitation on the present application.

Unless otherwise expressly indicated, the following terms used herein have the meanings indicated below.

The term "about" is used to describe and explain minor changes. When used in conjunction with an event or situation, this term may refer to examples where the event or situation occurs exactly and examples where the event or situation occurs very closely. For example, when used in conjunction with a numerical value, this term may refer to a variation range of less than or equal to ±10% of the numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. In addition, amounts, ratios and other numerical values are sometimes presented herein in a range format. It should be understood that such range formats are for convenience and brevity, and should be interpreted flexibly, and include not only those numerical values that are specifically designated as range limitations, but also include all individual numerical values or sub-ranges that are within the range, as each numerical value and sub-range is specified explicitly.

The term "hydrocarbyl" embraces alkyl, alkenyl and alkynyl.

The term "alkyl" is expected to be a linear saturated hydrocarbon structure having 1 to 20, 1 to 15, 1 to 10, 1 to 5 or 3 to 5 carbon atoms. "Alkyl" is also expected to be a branched or cyclic hydrocarbon structure having 3 to 20, 3 to 15, 3 to 10 or 3 to 5 carbon atoms. When an alkyl having a specific carbon number is specified, it is expected to cover all geometric isomers having that carbon number; therefore, for example, "butyl" means to include n-butyl, sec-butyl, isobutyl, tert-butyl and cyclobutyl; and "propyl" includes n-propyl, isopropyl and cyclopropyl. Examples of alkyl include, but are not limited to, methyl, ethyl, n-propyl, isopropyl, cyclopropyl, n-butyl, isobutyl, sec-butyl, tert-butyl, cyclobutyl, n-pentyl, isoamyl, neopentyl, cyclopentyl, methylcyclopentyl, ethylcyclopentyl, n-hexyl, isohexyl, cyclohexyl, n-heptyl, octyl, cyclopropyl, cyclobutyl, norbornyl and the like.

The term "alkenyl" refers to a monovalent unsaturated hydrocarbon group which may be linear or branched and has at least one and usually 1, 2 or 3 carbon-carbon double bonds. Unless otherwise defined, the alkenyl typically contains 2 to 20, 2 to 15, 2 to 10, 2 to 6, or 2 to 4 carbon atoms and includes, for example, —C$_{2-4}$ alkenyl, —C$_{2-6}$ alkenyl and —C$_{2-10}$ alkenyl. Representative alkenyl includes, for example, ethenyl, n-propenyl, isopropenyl, n-but-2-enyl, but-3-enyl, n-hex-3-enyl and the like.

The term "alkynyl" refers to a monovalent unsaturated hydrocarbon group which may be linear or branched and has at least one and usually 1, 2 or 3 carbon-carbon triple bonds. Unless otherwise defined, the alkynyl group typically contains 2 to 20, 2 to 15, 2 to 10, 3 to 10, 3 to 6, or 2 to 4 carbon atoms and includes, for example, —C$_{2-4}$ alkynyl, —C$_{3-6}$ alkynyl and —C$_{3-10}$ alkynyl. Representative alkynyl includes, for example, ethynyl, prop-2-ynyl (n-propynyl), n-but-2-ynyl, n-hex-3-ynyl and the like.

The term "alkylidene" refers to a divalent saturated hydrocarbon group which may be linear or branched. Unless otherwise defined, the alkylidene typically contains 1 to 10, 1 to 6, 1 to 4 or 2 to 4 carbon atoms and includes, for example, —$C_{2-3}$ alkylidene and —$C_{2-6}$ alkylidene-. Representative alkylidene includes, for example, methylene, ethane-1,2-diyl ("ethylidene"), propane-1,2-diyl, propane-1,3-diyl, butane-1,4-diyl, pentane-1,5-diyl and the like.

The term "alkenylene" refers to a difunctional group obtained by removing one hydrogen atom from the alkenyl defined above. Preferred alkenylene includes, but is not limited to, —CH=CH—, —C(CH$_3$)=CH—, —CH=CHCH$_2$— and the like. The term "aryl" refers to a monovalent aromatic hydrocarbon having a monocyclic (e.g., phenyl) or fused ring. Fused ring systems include completely unsaturated ring systems (e.g., naphthalene) and partially unsaturated ring systems (e.g., 1,2,3,4-tetrahydronaphthalene). Unless otherwise defined, the aryl typically contains 6 to 26, 6 to 20, 6 to 15, or 6 to 10 carbon ring atoms and includes, for example, —$C_{6-10}$ aryl. Representative aryl includes, for example, phenyl, methylphenyl, propylphenyl, isopropylphenyl, benzyl, naphthalen-1-yl, naphthalen-2-yl and the like.

The term "heteroatom" refers to an atom selected from N, O, P and S.

The term "heterocycle" or "heterocyclic group" refers to substituted or unsubstituted 5 to 8-membered monocyclic non-aromatic hydrocarbon or 5 to 8-membered bicyclic non-aromatic hydrocarbon, wherein 1 to 3 carbon atoms are replaced by heteroatom(s) selected from a nitrogen, oxygen, phosphorus or sulfur atom. Examples include pyrrolidin-2-yl; pyrrolidin-3-yl; piperidinyl; morpholin-4-yl and the like, and these groups can be substituted subsequently.

The term "halogen" refers to fluorine, chlorine, bromine or iodine.

The term "substituted or unsubstituted" means that a particular group is unsubstituted or substituted with one or more substituents.

As used herein, the content of each component is based on the total weight of the electrolyte.

1. Electrolyte

A first aspect of the present application provides an electrolyte, including a cyclic N-containing sulfonyl-compound and at least one of vinylene carbonate (VC), fluoroethylene carbonate (FEC), lithium tetrafluoroborate (LiBF$_4$), lithium difluoro(oxalato)borate (LiDFOB) or lithium difluorophosphate (LiPO$_2$F$_2$).

The inventors of the present application have surprisingly found that using the cyclic N-containing sulfonyl-compound in combination with at least one of electrolyte additives, such as vinylene carbonate (VC), fluoroethylene carbonate (FEC), lithium tetrafluoroborate (LiBF$_4$), lithium difluoro (oxalato)borate (LiDFOB) and lithium difluorophosphate (LiPO$_2$F$_2$), can significantly improve the high-temperature storage and cycle performance of an electrochemical device, such as a lithium-ion battery.

In some embodiments, the electrolyte of the present application includes the cyclic N-containing sulfonyl-compound and vinylene carbonate (VC). In some embodiments, the electrolyte of the present application includes the cyclic N-containing sulfonyl-compound, vinylene carbonate (VC) and lithium tetrafluoroborate (LiBF$_4$). In some embodiments, the electrolyte of the present application includes the cyclic N-containing sulfonyl-compound, vinylene carbonate (VC) and lithium difluoro(oxalato)borate (LiDFOB). In some embodiments, the electrolyte of the present application includes the cyclic N-containing sulfonyl-compound, vinylene carbonate (VC) and lithium difluorophosphate (LiPO$_2$F$_2$). In some embodiments, the electrolyte of the present application includes the cyclic N-containing sulfonyl-compound, vinylene carbonate (VC), lithium tetrafluoroborate (LiBF$_4$) and lithium difluoro(oxalato)borate (LiDFOB). In some embodiments, the electrolyte of the present application includes the cyclic N-containing sulfonyl-compound, vinylene carbonate (VC), lithium tetrafluoroborate (LiBF$_4$) and lithium difluorophosphate (LiPO$_2$F$_2$). In some embodiments, the electrolyte of the present application includes the cyclic N-containing sulfonyl-compound, vinylene carbonate (VC), lithium difluoro(oxalato)borate (LiDFOB) and lithium difluorophosphate (LiPO$_2$F$_2$). In some embodiments, the electrolyte of the present application includes the cyclic N-containing sulfonyl-compound, vinylene carbonate (VC), lithium tetrafluoroborate (LiBF$_4$), lithium difluoro(oxalato)borate (LiDFOB) and lithium difluorophosphate (LiPO$_2$F$_2$).

In some embodiments, the electrolyte of the present application includes the cyclic N-containing sulfonyl-compound and fluoroethylene carbonate (FEC). In some embodiments, the electrolyte of the present application includes the cyclic N-containing sulfonyl-compound, fluoroethylene carbonate (FEC) and lithium tetrafluoroborate (LiBF$_4$). In some embodiments, the electrolyte of the present application includes the cyclic N-containing sulfonyl-compound, fluoroethylene carbonate (FEC) and lithium difluoro (oxalato)borate (LiDFOB). In some embodiments, the electrolyte of the present application includes the cyclic N-containing sulfonyl-compound, fluoroethylene carbonate (FEC) and lithium difluorophosphate (LiPO$_2$F$_2$). In some embodiments, the electrolyte of the present application includes the cyclic N-containing sulfonyl-compound, fluoroethylene carbonate (FEC), lithium tetrafluoroborate (LiBF$_4$) and lithium difluoro(oxalato)borate (LiDFOB). In some embodiments, the electrolyte of the present application includes the cyclic N-containing sulfonyl-compound, fluoroethylene carbonate (FEC), lithium tetrafluoroborate (LiBF$_4$) and lithium difluorophosphate (LiPO$_2$F$_2$). In some embodiments, the electrolyte of the present application includes the cyclic N-containing sulfonyl-compound, fluoroethylene carbonate (FEC), lithium difluoro(oxalato)borate (LiDFOB) and lithium difluorophosphate (LiPO$_2$F$_2$). In some embodiments, the electrolyte of the present application includes the cyclic N-containing sulfonyl-compound, fluoroethylene carbonate (FEC), lithium tetrafluoroborate (LiBF$_4$), lithium difluoro(oxalato)borate (LiDFOB) and lithium difluorophosphate (LiPO$_2$F$_2$).

In some embodiments, the electrolyte of the present application includes the cyclic N-containing sulfonyl-compound, vinylene carbonate (VC) and fluoroethylene carbonate (FEC). In some embodiments, the electrolyte of the present application includes the cyclic N-containing sulfonyl-compound, vinylene carbonate (VC), fluoroethylene carbonate (FEC) and lithium tetrafluoroborate (LiBF$_4$). In some embodiments, the electrolyte of the present application includes the cyclic N-containing sulfonyl-compound, vinylene carbonate (VC), fluoroethylene carbonate (FEC) and lithium difluoro(oxalato)borate (LiDFOB). In some embodiments, the electrolyte of the present application includes the cyclic N-containing sulfonyl-compound, vinylene carbonate (VC), fluoroethylene carbonate (FEC) and lithium difluorophosphate (LiPO$_2$F$_2$). In some embodiments, the electrolyte of the present application includes the cyclic N-containing sulfonyl-compound, vinylene carbonate (VC), fluoroethylene carbonate (FEC), lithium tetrafluoroborate (LiBF$_4$) and lithium difluoro(oxalato)borate (LiDFOB). In some embodiments, the electrolyte of the present application includes the cyclic N-containing sulfonyl-compound, vinylene carbonate (VC), fluoroethylene carbonate (FEC), lithium tetrafluoroborate (LiBF$_4$) and lithium difluorophosphate (LiPO$_2$F$_2$). In some embodiments, the electrolyte of the present application includes the cyclic N-containing sulfonyl-compound, vinylene carbonate (VC), fluoroethylene carbonate (FEC), lithium difluoro(oxalato)borate (LiDFOB) and lithium difluorophosphate (LiPO$_2$F$_2$). In some embodiments, the electrolyte of the present application includes the cyclic N-containing sulfonyl-compound, vinylene carbonate (VC), fluoroethylene carbonate (FEC), lithium tetrafluoroborate (LiBF$_4$), lithium difluoro(oxalato)borate (LiDFOB) and lithium difluorophosphate (LiPO$_2$F$_2$).

Cyclic N-Containing Sulfonyl-Compound

In the electrolyte according to the present application, the cyclic N-containing sulfonyl-compound has excellent chemical stability, can form stable protective films on the surfaces of the anode and the cathode at the same time, can reduce side reactions of the electrolytes and the electrodes, and reduces dissolution of transition metal ions, thereby improving the high-temperature storage and cycle performance of an electrochemical device, such as a lithium-ion battery.

In some embodiments, the cyclic N-containing sulfonyl-compound is selected from the following compounds of Formula I,

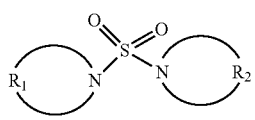

Formula I wherein R$_1$ and R$_2$ are each independently C$_3$-C$_5$ hydrocarbyl or C$_3$-C$_5$ heteroatomic hydrocarbyl containing 1-5 heteroatoms selected from N, O, P and S.

In some embodiments, the cyclic N-containing sulfonyl-compound includes, but is not limited to, at least one of the following compounds of Formula I-1 to Formula I-7:

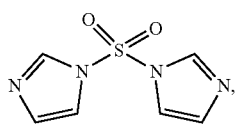

Formula I-1

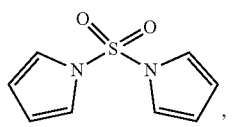

Formula I-2

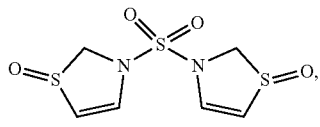

Formula I-3

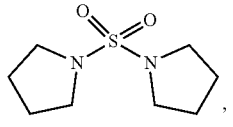

Formula I-4

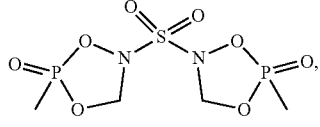

Formula I-5

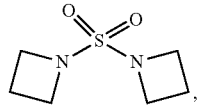

Formula I-6

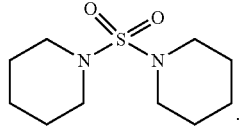

Formula I-7

In some embodiments, the cyclic N-containing sulfonyl-compound of the present application is N,N'-sulfonyldiimidazole.

In some embodiments, based on the total weight of the electrolyte, the content of the cyclic N-containing sulfonyl-compound is about 0.01 wt % to about 5 wt %. When the content of the cyclic N-containing sulfonyl-compound is within the range of about 0.01 wt % to about 5 wt %, sufficient protective films can be formed on the surfaces of the anode and the cathode, thereby improving the cycle performance and high-temperature storage performance of the electrochemical device (e.g., lithium-ion battery) and meanwhile also taking the first charge/discharge efficiency and dynamic performance of the electrochemical device (e.g., lithium-ion battery) into account.

In some embodiments, based on the total weight of the electrolyte, the upper limit of the content range of the cyclic N-containing sulfonyl-compound is selected from any of about 5 wt %, about 4 wt %, about 3 wt %, about 2 wt %, about 1 wt % and about 0.5 wt %, and the lower limit is selected from any of about 0.01 wt %, about 0.05 wt %, about 0.1 wt %, about 0.2 wt %, about 0.3 wt %, about 0.4 wt % and about 0.5 wt %. In some other embodiments, the content of the cyclic N-containing sulfonyl-compound in the electrolyte is about 0.5 wt % to about 5 wt %.

Vinylene Carbonate (VC)

In some embodiments, based on the total weight of the electrolyte, the content of the vinylene carbonate is about 0.001 wt % to about 4 wt %. When the content of the vinylene carbonate is within the range of about 0.001 wt % to about 4 wt %, a sufficient protective film can be formed on the surface of the cathode, thereby improving the cycle performance of the electrochemical device (e.g., lithium-ion battery) and meanwhile also taking the gas production performance under storage of the lithium-ion battery into account.

In some embodiments, based on the total weight of the electrolyte, the upper limit of the content range of the vinylene carbonate is selected from any of about 4 wt %, about 3 wt %, about 2 wt %, about 1 wt % and about 0.5 wt %, and the lower limit is selected from any of about 0.001 wt %, about 0.05 wt %, about 0.1 wt %, about 0.2 wt %, about 0.3 wt %, about 0.4 wt % and about 0.5 wt %. In some other embodiments, the content of the vinylene carbonate in the electrolyte is about 0.1 wt % to about 2 wt %.

Fluoroethylene Carbonate (FEC)

In some embodiments, based on the total weight of the electrolyte, the content of the fluoroethylene carbonate is about 0.1 wt % to about 10 wt %. When the content of the fluoroethylene carbonate is within the range of about 0.1 wt % to about 10 wt %, a sufficient protective film can be formed on the surface of the cathode, thereby improving the cycle performance of the electrochemical device (e.g., lithium-ion battery) and meanwhile also taking the gas production performance under storage of the lithium-ion battery into account.

In some embodiments, based on the total weight of the electrolyte, the upper limit of the content range of the fluoroethylene carbonate is selected from any of about 10 wt %, about 9 wt %, about 8 wt %, about 7 wt %, about 6 wt %, about 5 wt %, about 4 wt %, about 3 wt %, about 2 wt % and about 1 wt %, and the lower limit is selected from any of about 0.1 wt %, about 0.5 wt %, about 1 wt %, about 2 wt %, about 3 wt %, about 4 wt % and about 5 wt %. In some other embodiments, the content of the fluoroethylene carbonate in the electrolyte is about 1 wt % to about 5 wt %.

Lithium Tetrafluoroborate (LiBF$_4$)

In some embodiments, based on the total weight of the electrolyte, the content of the lithium tetrafluoroborate is about 0.001 wt % to about 2 wt %. When the content of the lithium tetrafluoroborate is within the range of about 0.001 wt % to about 2 wt %, a sufficient protective film can be formed on the surface of the cathode, thereby improving the cycle performance of the electrochemical device (e.g., lithium-ion battery) and meanwhile also taking the charging performance at low temperature into account.

In some embodiments, based on the total weight of the electrolyte, the upper limit of the content range of the lithium tetrafluoroborate is selected from any of about 2 wt %, about 1.5 wt %, about 1 wt % and about 0.8 wt %, and the lower limit is selected from any of about 0.001 wt %, about 0.01 wt %, about 0.05 wt %, about 0.1 wt % and about 0.5 wt %. In some other embodiments, the content of the lithium tetrafluoroborate in the electrolyte is about 0.1 wt % to about 1 wt %.

Lithium Difluoro(Oxalato)Borate (LiDFOB)

In some embodiments, based on the total weight of the electrolyte, the content of the lithium difluoro(oxalato)borate is about 0.001 wt % to about 2 wt %. When the content of the lithium difluoro(oxalato)borate is within the range of about 0.001 wt % to about 2 wt %, a sufficient protective film can be formed on the surface of the cathode, thereby improving the cycle performance of the electrochemical device (e.g., lithium-ion battery) and meanwhile also taking the charging performance at low temperature into account.

In some embodiments, based on the total weight of the electrolyte, the upper limit of the content range of the lithium difluoro(oxalato)borate is selected from any of about 2 wt %, about 1.5 wt %, about 1.2 wt %, about 1 wt % and about 0.8 wt %, and the lower limit is selected from any of about 0.001 wt %, about 0.005 wt %, about 0.1 wt %, about 0.3 wt % and about 0.5 wt %. In some other embodiments, the content of the lithium difluoro(oxalato)borate in the electrolyte is about 0.1 wt % to about 1 wt %.

Lithium difluorophosphate (LiPO$_2$F$_2$)

In some embodiments, based on the total weight of the electrolyte, the content of the lithium difluorophosphate is about 0.001 wt % to about 2 wt %. When the content of the lithium difluorophosphate is within the range of about 0.1 wt % to about 2 wt %, a sufficient protective film can be formed on the surface of the cathode, thereby improving the cycle performance of the electrochemical device (e.g., lithium-ion battery) and meanwhile also taking the charging performance at low temperature into account.

In some embodiments, based on the total weight of the electrolyte, the upper limit of the content range of the lithium difluorophosphate is selected from any of about 2 wt %, about 1.5 wt %, about 1.2 wt %, about 1 wt % and about 0.8 wt %, and the lower limit is selected from any of about 0.001 wt %, about 0.005 wt %, about 0.1 wt %, about 0.3 wt % and about 0.5 wt %. In some other embodiments, the content of the lithium difluorophosphate in the electrolyte is about 0.1 wt % to about 1 wt %.

Sulfur-Oxygen Double Bond Containing Compound

In some embodiments, the electrolyte of the present application may further include a sulfur-oxygen double bond containing compound to further enhance the protection to an active material.

In some embodiments, the sulfur-oxygen double bond containing compound of the present application includes, but is not limited to, at least one of the following compounds of Formula II-A, II-B or II-C:

(II-A)

(II-B)

(II-C)

wherein, $R_3$ and $R_4$ are each independently selected from substituted or unsubstituted $C_{1-5}$ alkyl, substituted or unsubstituted $C_{2-10}$ alkenyl, substituted or unsubstituted $C_{6-10}$ aryl or substituted or unsubstituted $C_{1-6}$ heterocyclic group; wherein, when substituted, they are substituted with one or more substituents selected from halogen, cyano, carboxy or sulfate group;

$R_5$ is selected from substituted or unsubstituted $C_{1-4}$ alkylidene, substituted or unsubstituted $C_{2-4}$ alkenylene, or substituted or unsubstituted $C_{1-6}$ chain alkane containing 1-5 heteroatoms selected from N, O, P and S, wherein, when substituted, they are substituted with one or more substituents selected from halogen, $C_{1-3}$ alkyl or $C_{2-4}$ alkenyl;

$R_6$ and $R_7$ are each independently selected from substituted or unsubstituted $C_{1-4}$ alkylidene, substituted or unsubstituted $C_{2-4}$ alkenylene, or substituted or unsubstituted $C_{1-6}$ chain alkane containing 1-5 heteroatoms selected from N, O, P and S, wherein, when substituted, they are substituted with one or more substituents selected from halogen, $C_{1-3}$ alkyl or $C_{2-4}$ alkenyl.

In some embodiments, the sulfur-oxygen double bond containing compound includes at least one of the following compounds of Formula II-1 to Formula II-8:

(II-1)

(II-2)

(II-3)

(II-4)

(II-5)

(II-6)

(II-7)

(II-8)

In some embodiments, the sulfur-oxygen double bond containing compound is methylene methanedisulfonate (Formula II-1, MMDS) and/or 1,3-propane sultone (Formula II-2, PS). In some embodiments, the sulfur-oxygen double bond containing compound is ethylene sulfate (Formula II-4, DTD) and/or 1,3-propane sultone (Formula II-2, PS). In some embodiments, the sulfur-oxygen double bond containing compound is ethylene sulfate (Formula II-4, DTD) and/or methylene methanedisulfonate (Formula II-1, MMDS).

In some embodiments, based on the total weight of the electrolyte, the content of the sulfur-oxygen double bond containing compound is about 0.01 wt % to about 10 wt %. When the content of the sulfur-oxygen double bond containing compound is within the range of about 0.01 wt % to about 10 wt %, complete and effective protective films can be formed on the surfaces of the anode and the cathode, thereby effectively preventing the side reaction caused by electron transfer between the non-aqueous electrolyte and the electrode, and meanwhile also taking the transport of lithium ions in the protective films into account.

In some embodiments, based on the total weight of the electrolyte, the upper limit of the content range of the sulfur-oxygen double bond containing compound is selected from any of about 10 wt %, about 5 wt %, about 4 wt %, about 3 wt %, about 2 wt %, about 1.5 wt %, about 1 wt % and about 0.5 wt %, and the lower limit is selected from any of about 0.01 wt %, about 0.1 wt %, about 0.3 wt %, about 0.5 wt % and about 0.6 wt %. In some other embodiments, the content of the sulfur-oxygen double bond containing compound in the non-aqueous electrolyte is about 0.1 wt % to about 5 wt %.

In some embodiments, the sulfur-oxygen double bond containing compound is 1,3-propane sultone (PS). Based on the total weight of the electrolyte, the content of the 1,3-propane sultone (PS) is about 0.1 wt % to about 5 wt %. In some embodiments, the sulfur-oxygen double bond containing compound is ethylene sulfate (DTD). Based on the total weight of the electrolyte, the content of the DTD is about 0.1 wt % to about 4 wt %. In some embodiments, the sulfur-oxygen double bond containing compound is methylene methanedisulfonate (MMDS). Based on the total weight of the electrolyte, the content of the MMDS is about 0.1 wt % to about 4 wt %.

Silicon-Containing Carbonate

In some embodiments, the electrolyte of the present application may further include a silicon-containing carbonate.

In some embodiments, the silicon-containing carbonate is selected from the following compounds of Formula III or Formula IV:

(III)

(IV)

wherein, $R_8$ and $R_9$ are each independently selected from $R^a$, —Si—(R")$_3$ or —R'—Si—(R")$_3$, and at least one of $R_8$ and $R_9$ contains Si;

$R^a$ and R" are each independently selected from H, $C_{1-12}$ alkyl, $C_{2-12}$ alkenyl, $C_{6-10}$ cyclohydrocarbyl or $C_{6-26}$ aryl; R' is selected from $C_{1-12}$ alkylidene or $C_{2-12}$ alkenylene; $R_8$ and $R_9$ are optionally substituted by halogen;

$R_{10}$ is C—$R^b$, and $R^b$ is selected from H, F, substituted or unsubstituted $C_{1-6}$ alkyl, or substituted or unsubstituted $C_{2-6}$ alkenyl; and $R_{11}$, $R_{12}$, $R_{13}$ and $R_{14}$ are independently selected from substituted or unsubstituted $C_{1-6}$ alkyl, substituted or unsubstituted $C_{1-6}$ alkoxy, substituted or unsubstituted $C_{2-6}$ alkenyl or substituted or unsubstituted $C_{6-10}$ aromatic ring, wherein the substituent is selected from halogen, $C_1$-$C_6$ alkyl or $C_2$-$C_6$ alkenyl.

According to some embodiments, the silicon-containing carbonate includes at least one of the following compounds of Formula III-1 to Formula III-5 and compounds of Formula IV-1 to Formula IV-3:

(III-1)

(III-2)

(III-3)

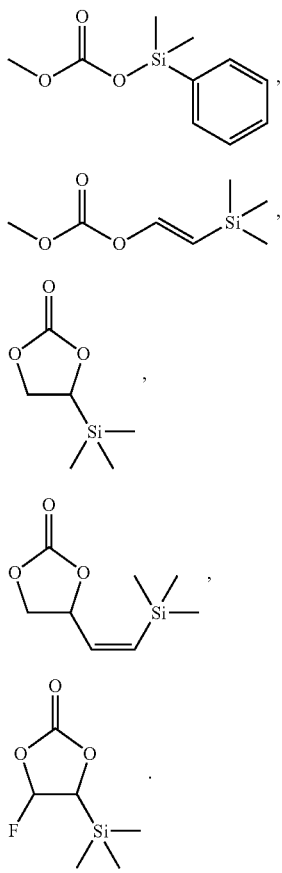

In some embodiments, the silicon-containing carbonate is a compound of Formula (III-1) and/or Formula (III-2).

In some embodiments, based on the total weight of the electrolyte, the content of the silicon-containing carbonate is about 0.1 wt % to about 20 wt %. When the content of the silicon-containing carbonate is within the range of about 0.1 wt % to about 20 wt %, a complete and an effective passivation layer can be formed on the surface of the cathode.

In some embodiments, based on the total weight of the electrolyte, the upper limit of the content range of the silicon-containing carbonate compound is selected from any of about 20 wt %, about 15 wt %, about 10 wt %, about 8 wt %, about 6 wt %, about 5 wt % and about 2 wt %, and the lower limit is selected from any of about 0.1 wt %, about 0.3 wt %, about 0.5 wt % and about 1 wt %. In some other embodiments, the content of the silicon-containing carbonate compound in the electrolyte is about 1 wt % to about 15 wt %.

In some embodiments, the non-aqueous electrolyte of the present application further includes an organic solvent and a lithium salt.

Organic Solvent

In some embodiments, the specific type of the organic solvent used in the present application is not limited. Preferably, the organic solvent used in the electrolyte of the present application may include: carbonates, for example, chain carbonates and cyclic carbonates; carboxylates, for example, chain carboxylates and cyclic carboxylates; and ethers, for example, chain ethers and cyclic ethers.

In some embodiments, examples of carbonates and carboxylates include, but are not limited to, one or more selected from dimethyl carbonate, ethyl methyl carbonate, methyl propyl carbonate, methyl isopropyl carbonate, methyl butyl carbonate, diethyl carbonate, dipropyl carbonate, dibutyl carbonate, ethylene carbonate, propylene carbonate, butylene carbonate, methyl acetate, ethyl acetate, propyl acetate, butyl acetate, methyl propionate, ethyl propionate, propyl propionate, butyl propionate, methyl butyrate, ethyl butyrate, propyl butyrate, methyl valerate, ethyl valerate, methyl pivalate, ethyl pivalate, butyl pivalate, γ-butyrolactone and γ-valerolactone.

In some embodiments, the chain ether includes, but is not limited to, one or more selected from dimethoxymethane, 1,1-dimethoxyethane, 1,2-dimethoxyethane, diethoxymethane, 1,1-diethoxyethane, 1,2-diethoxyethane, ethoxymethoxymethane, 1,1-ethoxymethoxyethane and 1,2-ethoxymethoxyethane.

In some embodiments, based on the total weight of the electrolyte, the content of the chain ether is about 0.1 wt % or more. In some embodiments, based on the total weight of the electrolyte, the content of the chain ether is about 0.5 wt % or more. In some embodiments, based on the total weight of the electrolyte, the content of the chain ether is about 2 wt % or more. In some embodiments, based on the total weight of the electrolyte, the content of the chain ether is about 3 wt % or more. In some embodiments, based on the total weight of the electrolyte, the content of the chain ether is about 10 wt % or less.

In some embodiments, the cyclic ether includes, but is not limited to, one or more selected from tetrahydrofuran, 2-methyltetrahydrofuran, 1,3-dioxolane, 2-methyl-1,3-dioxolane, 4-methyl-1,3-dioxolane, 1,3-dioxane, 1,4-dioxane and dimethoxypropane.

In some embodiments, based on the total weight of the electrolyte, the content of the cyclic ether is about 0.1 wt % or more. In some embodiments, based on the total weight of the electrolyte, the content of the cyclic ether is about 0.5 wt % or more. In some embodiments, based on the total weight of the electrolyte, the content of the cyclic ether is about 2 wt % or more. In some embodiments, based on the total weight of the electrolyte, the content of the cyclic ether is about 5 wt % or less.

In some embodiments, the organic solvent further includes a dinitrile compound, which is selected from one or a mixture of two or more of succinonitrile, adiponitrile, pimelonitrile, suberonitrile, 1,4-dicyano-2-butene, 1,4-dicyano-2-methyl-2-butene, 1,4-dicyano-2-ethyl-2-butene, 1,4-dicyano-2,3-dimethyl-2-butene, 1,4-dicyano-2,3-diethyl-2-butene, 1,6-dicyano-3-hexene, 1,6-dicyano-2-methyl-3-hexene and 1,6-dicyano-2-methyl-5-methyl-3-hexene.

In some embodiments, based on the total weight of the electrolyte, the content of the dinitrile compound is about 0.1 wt % or more. In some embodiments, based on the total weight of the electrolyte, the content of the dinitrile compound is about 0.5 wt % or more. In some embodiments, based on the total weight of the electrolyte, the content of the dinitrile compound is about 2 wt % or more. In some embodiments, based on the total weight of the electrolyte, the content of the dinitrile compound is about 4 wt % or more. In some embodiments, based on the total weight of the electrolyte, the content of the dinitrile compound is about 15 wt % or less. In some embodiments, based on the total weight of the electrolyte, the content of the dinitrile compound is about 10 wt % or less. In some embodiments, based on the total weight of the electrolyte, the content of the dinitrile compound is about 8 wt % or less. In some embodiments, based on the total weight of the electrolyte, the content of the dinitrile compound is about 0.1 wt % to about 15 wt %.

In some embodiments of the present application, the organic solvent further includes a phosphorus-containing organic solvent including, but not limited to, one or more selected from trimethyl phosphate, triethyl phosphate, dimethyl ethyl phosphate, methyl diethyl phosphate, ethylene methyl phosphate, ethylene ethyl phosphate, triphenyl phosphate, trimethyl phosphite, triethyl phosphite, triphenyl phosphite, tris(2,2,2-trifluoroethyl) phosphate and tris(2,2,3,3,3-pentafluoropropyl) phosphate.

In some embodiments, based on the total weight of the electrolyte, the content of the phosphorus-containing organic solvent is about 0.1 wt % or more. In some embodiments, based on the total weight of the electrolyte, the content of the phosphorus-containing organic solvent is about 0.5 wt % or more. In some embodiments, based on the total weight of the electrolyte, the content of the phosphorus-containing organic solvent is about 2 wt % or more. In some embodiments, based on the total weight of the electrolyte, the content of the phosphorus-containing organic solvent is about 3 wt % or more. In some embodiments, based on the total weight of the electrolyte, the content of the phosphorus-containing organic solvent is about 5 wt % or less.

In some embodiments of the present application, the organic solvent includes an aromatic fluorine-containing solvent including, but not limited to, one or more selected from fluorobenzene, difluorobenzene, trifluorobenzene, tetrafluorobenzene, pentafluorobenzene, hexafluorobenzene and trifluoromethylbenzene.

In some embodiments, based on the total weight of the electrolyte, the content of the aromatic fluorine-containing solvent is about 0.1 wt % or more. In some embodiments, based on the total weight of the electrolyte, the content of the aromatic fluorine-containing solvent is about 0.5 wt % or more. In some embodiments, based on the total weight of the electrolyte, the content of the aromatic fluorine-containing solvent is about 2 wt % or more. In some embodiments, based on the total weight of the electrolyte, the content of the aromatic fluorine-containing solvent is about 4 wt % or more. In some embodiments, based on the total weight of the electrolyte, the content of the aromatic fluorine-containing solvent is about 8 wt % or less.

Lithium Salt

In some embodiments, the lithium salt of the present application is selected from one or more of inorganic lithium salts and organic lithium salts. Preferably, the lithium salts are selected from one or more of lithium hexafluorophosphate ($LiPF_6$), lithium perchlorate, lithium bis(fluorosulfonyl)imide (LiFSI), lithium bis(trifluoromethanesulfonyl)imide (LiTFSI) and lithium bis(oxalato)borate (LiBOB). In some other embodiments, the lithium salt of the present application is selected from lithium hexafluorophosphate ($LiPF_6$).

In some embodiments, the concentration of the lithium salt is about 0.6 M to about 2 M. In some other embodiments, the concentration of the lithium salt is about 0.8 M to about 1.2 M.

The electrolyte according to the present application may be prepared by a conventional method, for example, mixing the materials in the electrolyte uniformly.

2. Electrochemical Device

A second aspect of the present application provides an electrochemical device, which comprises the electrolyte according to the present application.

The electrochemical device of the present application includes any device that generates an electrochemical reaction. The specific examples of the electrochemical device include all kinds of primary batteries, secondary batteries, fuel cells, solar cells, or capacitors. In particular, the electrochemical device is a lithium secondary battery, including a lithium metal secondary battery, a lithium-ion secondary battery, a lithium polymer secondary battery or a lithium-ion polymer secondary battery. In some embodiments, the electrochemical device is a lithium-ion battery.

In some embodiments, the electrochemical device of the present application includes a cathode, an anode and a separator, wherein the cathode contains a cathode active material and the anode contains a anode active material.

Cathode

In the electrochemical device according to the present application, the cathode includes a current collector and a cathode active material layer arranged on the current collector. The specific type of the cathode active material is not particularly limited and can be selected according to requirements.

For example, in some embodiments, the cathode active material includes a compound that reversibly intercalates and deintercalates lithium ions. In some embodiments, the cathode active material may include a composite oxide containing lithium and at least one element selected from cobalt, manganese and nickel. In some other embodiments, the cathode active material is selected from one or more of lithium cobalt oxide ($LiCoO_2$), lithium-nickel-manganese-cobalt ternary material, lithium manganate ($LiMn_2O_4$), lithium nickel manganese oxide ($LiNi_{0.5}Mn_{1.5}O_4$) and lithium iron phosphate ($LiFePO_4$).

In some embodiments, the cathode active material layer may have a coating on the surface or may be mixed with another compound having a coating.

The coating may include at least one coating element compound selected from an oxide of the coating element, a hydroxide of the coating element, an oxyhydroxide of the coating element, an oxycarbonate of the coating element and a hydroxycarbonate of the coating element.

The compound used for the coating may be amorphous or crystalline.

The coating element contained in the coating may include Mg, Al, Co, K, Na, Ca, Si, Ti, V, Sn, Ge, Ga, B, As, Zr, F or a mixture thereof.

The coating may be applied by any method as long as the method does not adversely affect the performance of the cathode active material. For example, the method may include any coating method well known to those of ordinary skill in the art, such as spraying, dipping, and the like.

In some embodiments, the cathode active material layer further includes a binder, and optionally further includes a conductive material.

The binder improves the binding among particles of the cathode active material, and also improves the binding between the cathode active material and the current collector. Non-limiting examples of the binder include polyvinyl alcohol, hydroxypropyl cellulose, diacetyl cellulose, polyvinyl chloride, carboxylated polyvinyl chloride, polyvinyl fluoride, ethylene oxide-containing polymers, polyvinylpyrrolidone, polyurethane, polytetrafluoroethylene, poly(1,1-difluoroethylene), polyethylene, polypropylene, styrene butadiene rubber, acrylated styrene butadiene rubber, epoxy resin, nylon, and the like.

The cathode active material layer includes the conductive material so as to impart conductivity to the electrode. The conductive material may include any conductive material as long as it does not cause a chemical change. Non-limiting examples of the conductive material include carbon-based materials (e.g., natural graphite, artificial graphite, carbon black, acetylene black, Ketjen black, carbon fibers, etc.), metal-based materials (e.g., metal powder, metal fibers, etc., including, for example, copper, nickel, aluminum, silver, etc.), conductive polymers (e.g., polyphenylene derivatives), and the mixtures thereof.

The current collector for the cathode of the secondary battery according to the present application may be aluminum (Al), but is not limited thereto.

Anode

In the electrochemical device according to the present application, the anode includes a current collector and an anode active material layer arranged on the current collector. The specific type of the anode active material is not particularly limited and can be selected according to requirements.

Specifically, in some embodiments, the anode active material is selected from one or more of natural graphite, artificial graphite, mesocarbon microbead (referred to as MCMB for short), hard carbon, soft carbon, silicon, silicon-carbon composite, Li—Sn alloy, Li—Sn—O alloy, Sn, SnO, $SnO_2$, lithiated $TiO_2$—$Li_4Ti_5O_{12}$ with a spinel structure and Li—Al alloy.

Non-limiting examples of carbon materials include crystalline carbon, amorphous carbon, and a mixture thereof. The crystalline carbon may be amorphous or flake-shaped, platelet-shaped, spherical or fibrous natural graphite or artificial graphite. The amorphous carbon may be soft carbon, hard carbon, mesophase pitch carbon composite, calcined coke, or the like.

In some embodiments, the anode active material layer may include a binder, and optionally further includes a conductive material.

The binder improves the binding among particles of the anode active material, and also improves the binding between the anode active material and the current collector. Non-limiting examples of the binder include polyvinyl alcohol, carboxymethyl cellulose, hydroxypropyl cellulose, diacetyl cellulose, polyvinyl chloride, carboxylated polyvinyl chloride, polyvinyl fluoride, ethylene oxide-containing polymers, polyvinylpyrrolidone, polyurethane, polytetrafluoroethylene, poly(1,1-difluoro ethylene), polyethylene, polypropylene, styrene butadiene rubber, acrylated styrene butadiene rubber, epoxy resin, nylon, and the like.

The anode active material layer includes the conductive material so as to impart conductivity to the electrode. The conductive material may include any conductive material as long as it does not cause a chemical change. Non-limiting examples of the conductive material include carbon-based materials (e.g., natural graphite, artificial graphite, carbon black, acetylene black, Ketjen black, carbon fibers, etc.), metal-based materials (e.g., metal powder, metal fibers, etc., including, for example, copper, nickel, aluminum, silver, etc.), conductive polymers (e.g., polyphenylene derivatives), and the mixtures thereof.

The current collector for the anode of the present application may be selected from copper foil, nickel foil, stainless steel foil, titanium foil, nickel foam, copper foam, a polymer substrate coated with a conductive metal, and combinations thereof.

Separator

In some embodiments, a separator is provided between the cathode and the anode of the electrochemical device of the present application to prevent short circuit. The material and shape of the separator used in the electrochemical device of the present application are not particularly limited, and may belong to any of the techniques disclosed in the prior art. In some embodiments, the separator includes a polymer or inorganic substance or the like formed of a material that is stable to the electrolyte of the present application.

For example, the separator may include a substrate layer and a surface treatment layer.

The substrate layer is a nonwoven fabric, a film or a composite film having a porous structure. The material of the substrate layer is at least one selected from polyethylene, polypropylene, polyethylene terephthalate and polyimide. Specifically, a polypropylene porous film, a polyethylene porous film, a polypropylene nonwoven fabric, a polyethylene nonwoven fabric or a polypropylene-polyethylene-polypropylene porous composite film may be used.

At least one surface of the substrate layer is provided with the surface treatment layer, and the surface treatment layer may be a polymer layer or an inorganic substance layer, or may be a layer formed by mixing a polymer and an inorganic substance.

The inorganic substance layer includes inorganic particles and a binder. The inorganic particles are selected from one or a combination of several of aluminum oxide, silicon oxide, magnesium oxide, titanium oxide, hafnium oxide, tin oxide, cerium oxide, nickel oxide, zinc oxide, calcium oxide, zirconium oxide, yttrium oxide, silicon carbide, boehmite, aluminum hydroxide, magnesium hydroxide, calcium hydroxide and barium sulfate. The binder is selected from one or a combination of several of polyvinylidene fluoride, a vinylidene fluoride-hexafluoropropylene copolymer, polyamide, polyacrylonitrile, polyacrylate, polyacrylic acid, polyacrylate, polyvinylpyrrolidone, polyvinyl ether, polymethyl methacrylate, polytetrafluoroethylene and polyhexafluoropropylene.

The polymer layer includes a polymer. The material of the polymer is at least one selected from polyamide, polyacrylonitrile, acrylate polymer, polyacrylic acid, polyacrylate, polyvinylpyrrolidone, polyvinyl ether, polyvinylidene fluoride and poly(vinylidene fluoride-hexafluoropropylene).

3. Electronic Device

Another aspect of the present application provides an electronic device, which includes the electrochemical device of the present application.

The electrochemical device according to the present application is suitable for use in electronic equipment in various fields. The use of the electrochemical device of the present application is not particularly limited and can be used in any use known in the prior art. In an embodiment, the electrochemical device of the present application may be used for, but not limited to, the following electronic devices: a notebook computer, a pen input computer, a mobile computer, an e-book player, a portable phone, a portable fax machine, a portable copy machine, a portable printer, stereo headphones, a video recorder, a liquid crystal display television, a portable cleaner, a portable CD player, a mini disk player, a transceiver, an electronic notebook, a calculator, a memory card, a portable recorder, a radio, a backup power device, a motor, a car, a motorcycle, a power bicycle, a bicycle, a lighting fixture, a toy, a game console, a clock, an electric tool, a flashlight, a camera, a large household storage battery, a lithium-ion capacitor and the like.

EXAMPLES

The embodiments of the present application will be illustrated below with examples. It should be understood that these examples are only for illustrating the present application and are not intended to limit the claimed scope of the present application.

Preparation Method

The Lithium-Ion Batteries of Examples 1-54 and Comparative Examples 1-6 were all Prepared as Follows:

(1) Preparation of Cathode

A cathode active material of lithium-nickel-manganese-cobalt ternary material (NCM523), a conductive agent of Super P, and a binder of polyvinylidene fluoride were mixed in a weight ratio of 97:1.4:1.6. N-methylpyrrolidone (NMP) was added thereto. The system was uniformly stirred by means of a vacuum mixer to obtain a cathode slurry, wherein the solid content of the cathode slurry was 72 wt %. The cathode slurry was uniformly coated on a cathode current collector of the cathode, i.e., an aluminum foil, and dried at 85° C. Then, it was subjected to cold pressing, cutting and slitting, followed by drying under vacuum at 85° C. for 4 hours to obtain a cathode.

(2) Preparation of Anode

A anode active material of artificial graphite, a conductive agent of Super P, a thickener of sodium carboxymethyl cellulose (CMC) and a binder of styrene-butadiene rubber (SBR) were mixed in a weight ratio of 96.4:1.5:0.5:1.6. Deionized water was added thereto. A anode slurry was obtained by means of a vacuum mixer, wherein the solid content of the anode slurry was 54 wt %. The anode slurry was uniformly coated on an anode current collector of the anode, i.e., a copper foil, and dried at 85° C. Then, it was subjected to cold pressing, cutting and slitting, followed by drying under vacuum at 120° C. for 12 hours to obtain a anode.

(3) Preparation of Electrolyte

In a dry argon atmosphere glove box, ethylene carbonate (EC), ethyl methyl carbonate (EMC) and diethyl carbonate (DEC) were mixed in a weight ratio of EC:EMC:DEC=30:50:20. Then, an additive was added, dissolved and thoroughly stirred, followed by adding a lithium salt $LiPF_6$. An electrolyte was obtained after mixing uniformly, wherein the concentration of the $LiPF_6$ was 1 mol/L. The specific types and contents of the additives used in the electrolyte are shown in Table 1. In Table 1, the content of the additive is a weight percentage calculated based on the total weight of the electrolyte.

(4) Preparation of Separator A 7 μm thick polyethylene (PE) separator was used.

(5) Preparation of Lithium-Ion Battery

The cathode, the separator and the anode were stacked in order such that the separator was positioned between the cathode and anode for separation. A cell was obtained by winding. After welding on tabs, the cell was placed in the outer packing of aluminum foil-plastic film. The prepared electrolyte was poured into the dried cell. Then, it was subjected to the processes such as vacuum encapsulation, standing, formation (charging at a constant current of 0.02 C to 3.3 V, and then charging at a constant current of 0.1 C to 3.6 V), shaping, capacity testing and so on to obtain the lithium-ion battery.

TABLE 1

Parameters of electrolytes in Comparative Examples 1-3 and Examples 1-27

| Example | FEC (wt %) | VC (wt %) | LiDFOB (wt %) | $LiPO_2F_2$ (wt %) | $LiBF_4$ (wt %) | Formula I-1 (wt %) | Formula I-2 (wt %) | Formula I-3 (wt %) |
|---|---|---|---|---|---|---|---|---|
| Comparative Example 1 | — | — | — | — | — | — | — | — |
| Comparative Example 2 | — | — | — | — | — | 0.5 | — | — |
| Comparative Example 3 | 3 | — | — | — | — | — | — | — |
| Examples 1 | 3 | — | — | — | — | 0.1 | — | — |
| Examples 2 | 3 | — | — | — | — | 0.5 | — | — |
| Example 3 | 3 | — | — | — | — | 1 | — | — |
| Example 4 | 3 | — | — | — | — | 2 | — | — |
| Example 5 | 3 | — | — | — | — | 3 | — | — |
| Example 6 | 0.5 | — | — | — | — | 0.5 | — | — |
| Example 7 | 1 | — | — | — | — | 0.5 | — | — |
| Example 8 | 2 | — | — | — | — | 0.5 | — | — |
| Example 9 | 5 | — | — | — | — | 0.5 | — | — |
| Example 10 | 8 | — | — | — | — | 0.5 | — | — |
| Example 11 | 3 | — | — | — | — | — | 0.5 | — |
| Example 12 | 3 | — | — | — | — | — | — | 0.5 |
| Example 13 | 3 | 0.3 | — | — | — | 0.5 | — | — |
| Example 14 | 3 | — | 0.5 | — | — | 0.5 | — | — |
| Example 15 | 3 | 0.1 | — | — | — | 0.5 | — | — |
| Example 16 | 3 | — | — | 0.5 | — | 0.5 | — | — |
| Example 17 | 3 | — | 0.5 | — | — | — | 0.5 | — |
| Example 18 | 3 | 0.9 | 0.5 | — | — | — | 0.5 | — |
| Example 19 | 3 | — | — | — | — | 0.1 | — | 0.5 |
| Example 20 | 3 | — | 0.5 | — | — | — | — | 0.5 |
| Example 21 | — | 0.9 | — | — | — | — | — | 0.5 |
| Example 22 | 3 | — | 0.5 | — | — | 0.5 | 0.1 | — |
| Example 23 | — | 0.9 | 0.5 | — | — | 0.5 | — | — |
| Example 24 | 3 | 0.1 | — | 0.5 | — | 0.5 | — | — |
| Example 25 | 3 | 0.9 | — | 0.5 | — | 0.5 | — | 0.1 |
| Example 26 | 3 | — | — | — | 0.1 | 0.5 | — | — |
| Example 27 | — | 0.9 | — | — | 0.1 | 0.5 | — | — |

Test Methods

The lithium-ion batteries prepared in the examples of the present application were tested by using the following methods.

(1) Cycle Performance Test of the Lithium-Ion Battery

The process for cycle test at 25° C.:

The lithium-ion battery was placed in a calorstat oven at 25° C. and allowed to stand for 30 minutes to allow the lithium-ion battery reach a constant temperature. The battery was charged at a constant current of 1 C to a voltage of 4.4 V, then charged at a constant voltage of 4.4 V to a current of 0.05 C, and discharged at a constant current of 1 C to a voltage of 2.8 V, which was one charge and discharge cycle. The first discharge capacity was recorded. The charge and discharge cycle was performed by taking the first discharge capacity as 100%. When the discharge capacity was reduced to 80%, the test was stopped. The cycle number was recorded as an index for evaluating the cycle performance of the lithium-ion battery.

The process for cycle test at 45° C.:

The lithium-ion battery was placed in a calorstat oven at 45° C. and allowed to stand for 30 minutes to allow the lithium-ion battery reach a constant temperature. The battery was charged at a constant current of 1 C to a voltage of 4.4 V, then charged at a constant voltage of 4.4 V to a current of 0.05 C, and discharged at a constant current of 1 C to a voltage of 2.8 V, which was one charge and discharge cycle. The first discharge capacity was recorded. The charge and discharge cycle was performed by taking the first discharge capacity as 100%. When the discharge capacity was reduced to 80%, the test was stopped. The cycle number was recorded as an index for evaluating the cycle performance of the lithium-ion battery.

(2) Test of the Storage Performance at High Temperature of Lithium-Ion Battery

The lithium-ion battery was placed in a 25° C. environment and allowed to stand for 30 minutes to allow the lithium-ion battery reach a constant temperature. The battery was discharged at a constant current of 0.5 C to 4.4 V and charged at a constant voltage to a current of 0.05 C. The thickness of the battery was tested with an automatic thickness gauge and recorded. The above battery was transferred to an oven at 60° C. and stored at a constant temperature for 30 days, during which the thickness of the battery was tested every 3 days. The battery was taken out of the oven at 60° C., and transferred to a 25° C. environment. The thickness test was completed within 10 minutes. After testing the thickness, the battery was transferred to the oven at 60° C. and the test continued. The thickness variation of the battery was monitored during the storage process.

Thickness expansion ratio=(the storage thickness at 60° C.—the initial thickness)/the initial thickness×100%

(3) Over-Charge Test of the Lithium-Ion Battery

The battery was charged in a 25° C. environment at a constant current of 2 C to 6.5 V, and then further charged at a constant voltage of 6.5 V for 3 hours. The appearance changes of the battery were monitored. The evaluating criterions were: no ignition, no burning and no explosion. 10 batteries were tested and the number of the batteries passed said test was recorded.

TABLE 2

Performance test results for Comparative Examples 1-3 and Examples 1-27

|  | Cycle Number at 25° C. | Cycle Number at 45° C. | Thickness Expansion Rate Stored at 60° C. (%) |
| --- | --- | --- | --- |
| Comparative Example 1 | 255 | 126 | 53 |
| Comparative Example 2 | 475 | 388 | 20 |
| Comparative Example 3 | 325 | 267 | 50 |
| Examples 1 | 525 | 489 | 22 |
| Examples 2 | 769 | 568 | 18 |
| Example 3 | 777 | 576 | 10 |
| Example 4 | 725 | 551 | 6 |
| Example 5 | 671 | 537 | 5 |
| Example 6 | 665 | 538 | 14 |
| Example 7 | 690 | 548 | 14 |
| Example 8 | 734 | 579 | 15 |
| Example 9 | 745 | 580 | 28 |
| Example 10 | 741 | 578 | 28 |
| Example 11 | 760 | 548 | 12 |
| Example 12 | 751 | 571 | 16 |
| Example 13 | 809 | 631 | 15 |
| Example 14 | 807 | 618 | 10 |
| Example 15 | 782 | 587 | 15 |
| Example 16 | 821 | 635 | 10 |
| Example 17 | 806 | 611 | 9 |
| Example 18 | 811 | 626 | 10 |
| Example 19 | 781 | 568 | 12 |
| Example 20 | 801 | 611 | 8 |
| Example 21 | 765 | 580 | 10 |
| Example 22 | 812 | 622 | 9 |
| Example 23 | 801 | 635 | 8 |
| Example 24 | 809 | 627 | 9 |
| Example 25 | 810 | 623 | 8 |
| Example 26 | 790 | 618 | 6 |
| Example 27 | 791 | 621 | 5 |

By analyzing the data in Table 1 and Table 2, it can be known that the combination of at least one of the cyclic N-containing sulfonyl-compounds with at least one of FEC, VC, LiDFOB, $LiPO_2F_2$ and $LiBF_4$ can improve the cycle performance and high-temperature storage performance of the battery.

TABLE 3

Parameters of electrolytes in Comparative Example 2 and Examples 2 and 28-38

|  | FEC (wt %) | Formula I-1 (wt %) | Formula I-2 (wt %) | Formula I-3 (wt %) | Formula II-1 (wt %) | Formula II-2 (wt %) |
| --- | --- | --- | --- | --- | --- | --- |
| Example 2 | 3 | 0.5 | — | — | — | — |
| Comparative Example 2 | — | 0.5 | — | — | — | — |
| Example 28 | 3 | 0.5 | — | — | 0.1 | — |
| Example 29 | 3 | 0.5 | — | — | 0.3 | — |
| Example 30 | 3 | 0.5 | — | — | 0.5 | — |
| Example 31 | 3 | 0.5 | — | — | 0.9 | — |

TABLE 3-continued

Parameters of electrolytes in Comparative Example 2 and Examples 2 and 28-38

|  | FEC (wt %) | Formula I-1 (wt %) | Formula I-2 (wt %) | Formula I-3 (wt %) | Formula II-1 (wt %) | Formula II-2 (wt %) |
| --- | --- | --- | --- | --- | --- | --- |
| Example 32 | 3 | 0.5 | — | — | 1 | — |
| Example 33 | 3 | 0.5 | — | — | 2 | — |
| Example 34 | 3 | 0.5 | — | — | 4 | — |
| Example 35 | 3 | — | 0.5 | — | 1 | — |
| Example 36 | 3 | — | — | 0.5 | 1 | — |
| Example 37 | 3 | 0.5 | — | — | — | 3 |
| Example 38 | 3 | 0.5 | — | — | 1 | 3 |

TABLE 4

Performance test results for Comparative Example 2 and Examples 2 and 28-38

|  | Cycle Number at 25° C. | Cycle Number at 45° C. | Thickness Expansion Rate Stored at 60° C. (%) |
| --- | --- | --- | --- |
| Example 2 | 769 | 568 | 18 |
| Comparative Example 2 | 475 | 388 | 20 |
| Example 28 | 575 | 388 | 17 |
| Example 29 | 776 | 579 | 14 |
| Example 30 | 787 | 588 | 12 |
| Example 31 | 803 | 601 | 10 |
| Example 32 | 810 | 611 | 8 |
| Example 33 | 817 | 615 | 7 |
| Example 34 | 819 | 619 | 7 |
| Example 35 | 815 | 618 | 7 |
| Example 36 | 811 | 623 | 9 |
| Example 37 | 807 | 621 | 9 |
| Example 38 | 813 | 615 | 7 |

It can be seen from Examples 28-38 that the combination of the cyclic N-containing sulfonyl-compound with the compound containing a sulfur-oxygen double bond functional group can further improve the cycle performance and high-temperature storage performance, which is mainly due to the fact that the sulfur-oxygen double bond functional group can further form stable sulfite SEI films on the surfaces of the anode and the cathode.

As an improvement, a carbonate compound containing a silicon functional group may also be added to the electrolyte of the present application, which can have the function of further improving the high-temperature storage performance and over-charge performance. The following Examples 39-47 illustrate the use of the cyclic N-containing sulfonyl-compound in combination with the silicon-containing carbonate.

TABLE 5

Parameters of electrolytes of Comparative Example 2 and Examples 2 and 39-47

|  | FEC (wt %) | Formula I-1 (wt %) | Formula I-2 (wt %) | Formula III-1 (wt %) | Formula III-2 (wt %) |
| --- | --- | --- | --- | --- | --- |
| Example 2 | 3 | 0.5 | — | — | — |
| Comparative Example 2 | — | 0.5 | — | — | — |
| Example 39 | 3 | 0.5 | — | 1 | — |
| Example 40 | 3 | 0.5 | — | 3 | — |
| Example 41 | 3 | 0.5 | — | 5 | — |
| Example 42 | 3 | 0.5 | — | 7 | — |
| Example 43 | 3 | 0.5 | — | 10 | — |
| Example 44 | 3 | 0.5 | — | 15 | — |
| Example 45 | 3 | 0.5 | — | 20 | — |
| Example 46 | 3 | — | 0.5 | 10 | — |
| Example 47 | 3 | 0.5 | — | — | 10 |

TABLE 6

Battery performance test results of electrolytes of Comparative Example 2 and Examples 2 and 39-47

|  | Cycle Number at 25° C. | Cycle Number at 45° C. | Thickness Expansion Rate Stored at 60° C. (%) | Over-charge (10 batteries) |
| --- | --- | --- | --- | --- |
| Example 2 | 769 | 568 | 18 | 3 |
| Comparative Example 2 | 475 | 388 | 20 | 2 |
| Example 39 | 765 | 578 | 13 | 2 |
| Example 40 | 775 | 587 | 11 | 3 |
| Example 41 | 783 | 592 | 8 | 5 |
| Example 42 | 790 | 608 | 6 | 7 |
| Example 43 | 801 | 615 | 5 | 10 |
| Example 44 | 813 | 618 | 5 | 10 |
| Example 45 | 809 | 610 | 5 | 10 |
| Example 46 | 817 | 619 | 6 | 10 |
| Example 47 | 802 | 614 | 6 | 10 |

From the comparison between Examples 39-47 and Example 2, it can be seen that the combination of the cyclic N-containing sulfonyl-compound and the silicon-containing carbonate can significantly improve the high-temperature storage and over-charge performance and meanwhile improve the high-temperature cycle performance.

As an improvement of the non-aqueous electrolyte of the present application, the fluoroethylene carbonate, cyclic N-containing sulfonyl-compound, sulfur-oxygen double bond containing compound, lithium difluoro(oxalato)borate, lithium difluorophosphate and silicon-containing carbonate may also be added at the same time in the present application to further enhance the protection from the anode active material and the cathode, and meanwhile improve the overall performance of the battery. The specific combinations are preferably as follows, but are not limited thereto:

TABLE 7

Parameters of electrolytes of Comparative Examples 4-6 and Examples 48-54

| | FEC (wt %) | LiDFOB (wt %) | LiPO$_2$F$_2$ (wt %) | Formula I-1 (wt %) | Formula I-2 (wt %) | Formula II-1 MMDS (wt %) | Formula II-2 PS (wt %) | Formula III-1 (wt %) |
|---|---|---|---|---|---|---|---|---|
| Comparative Example 3 | 3 | — | — | — | — | — | — | — |
| Comparative Example 4 | 3 | — | — | — | — | — | — | 10 |
| Comparative Example 5 | 3 | — | — | — | — | 1 | — | — |
| Comparative Example 6 | 3 | — | — | — | — | — | 3 | — |
| Example 2 | 3 | — | — | 0.5 | — | — | — | — |
| Example 48 | 3 | — | — | 0.5 | — | — | 3 | 5 |
| Example 49 | 3 | — | 0.5 | 0.5 | — | 1 | — | — |
| Example 50 | 3 | — | — | 0.5 | — | 1 | 3 | — |
| Example 51 | 3 | — | — | 0.5 | — | 1 | 3 | 10 |
| Example 52 | 3 | 0.5 | — | 0.5 | — | 1 | 3 | 10 |
| Example 53 | 3 | — | 0.5 | 0.5 | — | 1 | 3 | 10 |
| Example 54 | 3 | 0.5 | — | — | 0.5 | 1 | 3 | 10 |

TABLE 8

Performance test results of the battery comprising the electrolytes of Comparative Examples 3-6 and Examples 2 and 48-54

| Example | Cycle Number at 25° C. | Cycle Number at 45° C. | Thickness Expansion Rate Stored at 60° C. (%) | Over-charge (10 batteries) |
|---|---|---|---|---|
| Comparative Example 3 | 325 | 267 | 50 | 1 |
| Comparative Example 4 | 425 | 346 | 33 | 7 |
| Comparative Example 5 | 500 | 355 | 20 | 3 |
| Comparative Example 6 | 460 | 336 | 15 | 3 |
| Example 2 | 769 | 568 | 18 | 3 |
| Example 48 | 823 | 635 | 7 | 9 |
| Example 49 | 835 | 638 | 13 | 4 |
| Example 50 | 837 | 641 | 8 | 4 |
| Example 51 | 844 | 653 | 4 | 10 |
| Example 52 | 862 | 667 | 4 | 10 |
| Example 53 | 858 | 665 | 5 | 10 |
| Example 54 | 886 | 686 | 4 | 10 |

When referring to "embodiments", "some embodiments", "an embodiment", "another example", "examples", "specific examples" or "partial examples" in the specification of the present application, it means that at least one embodiment or example of the embodiments of the present application includes the specific features, structures, materials or characteristics described in the embodiments or examples. Therefore, descriptions appearing throughout the specification, such as "in some embodiments", "in the embodiments", "in an embodiment", "in another example", "in an example", "in a particular example" or "examples", are not necessarily referring to the same embodiments or examples in the embodiments of the present application. Furthermore, the particular features, structures, materials or characteristics herein may be combined in any suitable manner in one or more embodiments or examples.

The above description summarizes the features of several embodiments, which will enable those of ordinary skill in the art to understand the various aspects of the present application. Those of ordinary skill in the art can readily use the present application as a basis for designing or modifying other compositions to achieve the same objectives and/or the same advantages as the embodiments herein. It is also to be understood by those of ordinary skill in the art that these equivalent examples do not depart from the spirit and scope of the present application, and it is possible to make various changes, substitutions and modifications to the present application without departing from the spirit and scope of the present application. Although the methods disclosed herein have been described with reference to the specific operations that are carried out in a specific order, it should be understood that these operations can be combined, subdivided, or reordered to form an equivalent method without departing from the teachings of the present application. Therefore, the order and grouping of operations are not a limitation to the present application unless specifically indicated herein.

What is claimed is:

1. An electrolyte, comprising:
at least one cyclic N-containing sulfonyl-compound according to Formula I-1, Formula I-2, Formula I-3, or Formula I-5:

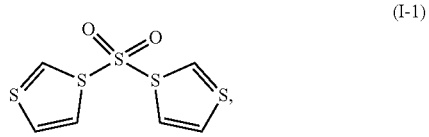

(I-1)

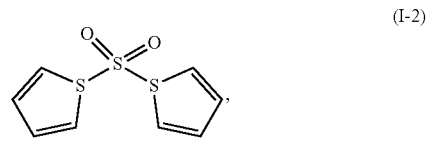

(I-2)

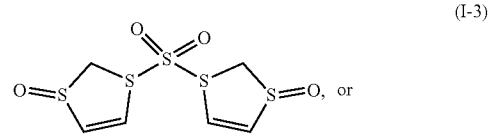

(I-3)

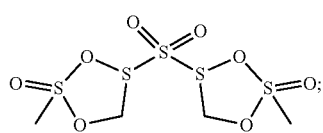
(I-5)

at least one of vinylene carbonate, fluoroethylene carbonate, lithium tetrafluoroborate, lithium difluoro(oxalate)borate or lithium difluorophosphate;

a silicon-containing carbonate selected from the following compounds of Formula III or Formula IV:

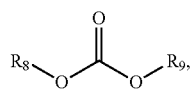
(III)

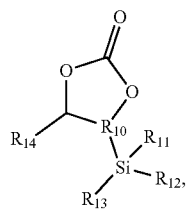
(IV)

wherein, $R_8$ and $R_9$ are each independently selected from $R^a$, —Si—$(R'')_3$ or —R'—Si—$(R'')_3$, and at least one of $R_8$ and $R_9$ contains Si;

$R^a$ and $R''$ are each independently selected from H, $C_{1-12}$ alkyl, $C_{2-12}$ alkenyl, $C_{6-10}$ cyclohydrocarbyl or $C_{6-26}$ aryl;

R' is selected from $C_{1-12}$ alkylidene or $C_{2-12}$ alkenylene;

$R_{10}$ is C—$R^b$, and $R^b$ is selected from H, F, substituted or unsubstituted $C_{1-6}$ alkyl, or substituted or unsubstituted $C_{2-6}$ alkenyl, and $R_{11}$, $R_{12}$, $R_{13}$ and $R_{14}$ are independently selected from substituted or unsubstituted $C_{1-6}$ alkyl, substituted or unsubstituted $C_{1-6}$ alkoxy, substituted or unsubstituted $C_{2-6}$ alkenyl or substituted or unsubstituted $C_{6-10}$ aromatic ring, wherein, the substituent is selected from halogen, $C_{1-6}$ alkyl or $C_{2-6}$ alkenyl; and wherein the at least one cyclic N-containing sulfonyl-compound further comprises at least one of the following compounds of Formula I-4, Formula I-6, and Formula I-7:

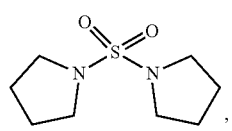
(I-4)

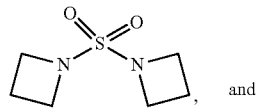
and
(I-6)

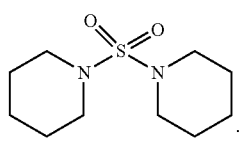
(I-7)

2. The electrolyte according to claim 1, further comprising a sulfur-oxygen double bond containing compound, wherein the sulfur-oxygen double bond containing compound comprises at least one of the following compounds of Formula II-A, II-B or II-C:

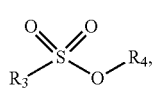
(II-A)

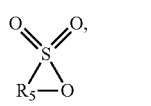
(II-B)

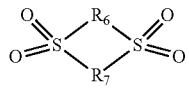
(II-C)

wherein, $R_3$ and $R_4$ are each independently selected from substituted or unsubstituted $C_{1-5}$ alkyl, substituted or unsubstituted $C_{2-10}$ alkenyl, substituted or unsubstituted $C_{6-10}$ aryl, or substituted or unsubstituted $C_{1-6}$ heterocyclic group; wherein, when substituted, they are substituted with one or more substituents selected from halogen, cyano, carboxy or sulfate group;

$R_5$ is selected from substituted or unsubstituted $C_{1-4}$ alkylidene, substituted or unsubstituted $C_{2-4}$ alkenylene, or substituted or unsubstituted $C_{1-6}$ chain alkane containing 1-5 heteroatoms selected from N, O, P and S, wherein, when substituted, they are substituted with one or more substituents selected from halogen, $C_{1-3}$ alkyl or $C_{2-4}$ alkenyl; and $R_6$ and $R_7$ are each independently selected from substituted or unsubstituted $C_{1-4}$ alkylidene, substituted or unsubstituted $C_{2-4}$ alkenylene, or substituted or unsubstituted $C_{1-6}$ chain alkane containing 1-5 heteroatoms selected from N, O, P and S, wherein, when substituted, they are substituted with one or more substituents selected from halogen, $C_{1-3}$ alkyl or $C_{2-4}$ alkenyl.

3. The electrolyte according to claim 2, wherein the sulfur-oxygen double bond containing compound comprises at least one of the following compounds of Formula II-1 to Formula II-8:

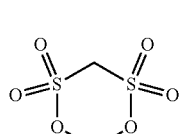
(II-1)

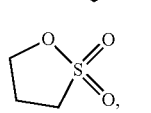
(II-2)

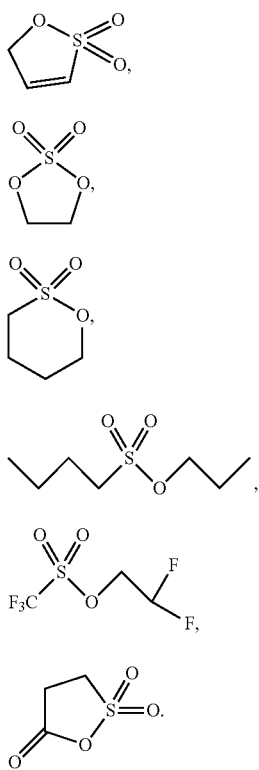

4. The electrolyte according to claim 2, wherein based on the total weight of the electrolyte, the content of the sulfur-oxygen double bond containing compound is about 0.01 wt % to about 10 wt %.

5. The electrolyte according to claim 1, wherein the silicon-containing carbonate comprises at least one of the following compounds of Formula III-1 to Formula III-5 and compounds of Formula IV-1 to Formula IV-3:

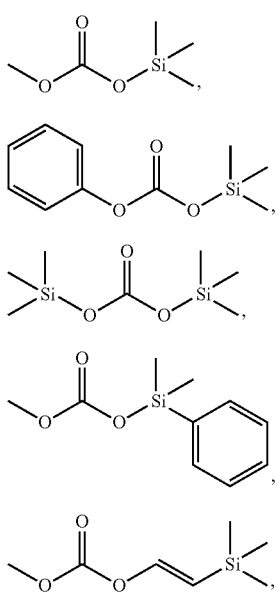

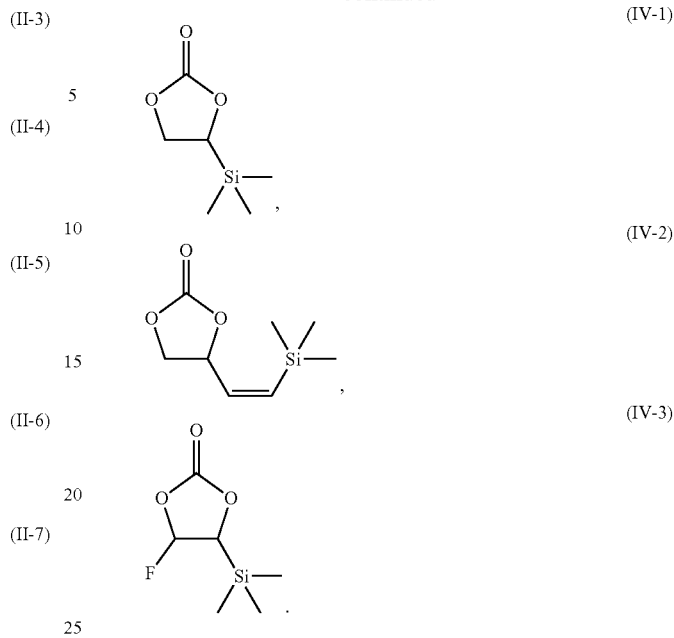

6. The electrolyte according to claim 1, wherein based on the total weight of the electrolyte,
the content of the at least one cyclic N-containing sulfonyl-compound is about 0.01 wt % to about 5 wt %,
the content of the vinylene carbonate is about 0.001 wt % to about 4 wt %,
the content of the fluoroethylene carbonate is about 0.1 wt % to about 10 wt %,
the content of the lithium tetrafluoroborate is about 0.001 wt % to about 2 wt %,
the content of the lithium difluoro(oxalate)borate is about 0.001 wt % to about 2 wt %, and
the content of the lithium difluorophosphate is about 0.001 wt % to about 2 wt %.

7. The electrolyte according to claim 1, wherein based on the total weight of the electrolyte, the content of the silicon-containing carbonate is about 0.1 wt % to about 20 wt %.

8. An electrochemical device, comprising:
an electrolyte comprising:
at least one cyclic N-containing sulfonyl-compound of Formula I-1, Formula I-2, Formula I-3, or Formula I-5:

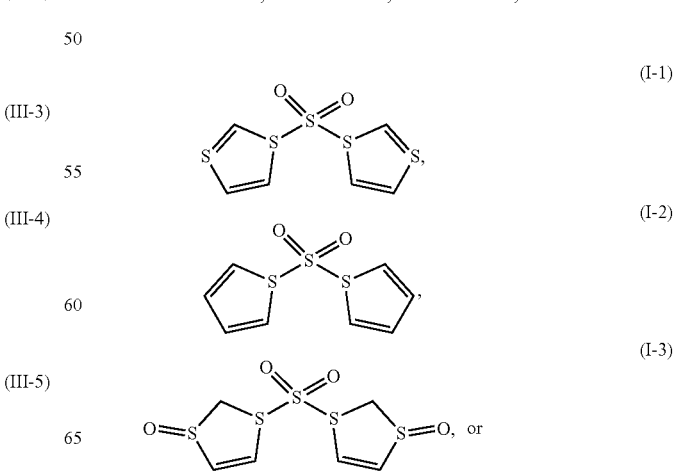

-continued (I-5)
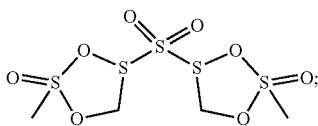

(I-7)
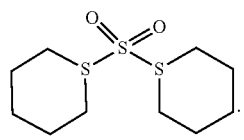

at least one of vinylene carbonate, fluoroethylene carbonate, lithium tetrafluoroborate, lithium difluoro(oxalate)borate or lithium difluorophosphate; and a silicon-containing carbonate selected from the following compounds of Formula III or Formula IV:

(III)

R$_8$\O\C(=O)\O\R$_9$, (IV)

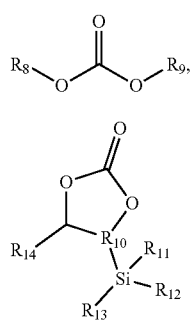

wherein,

- R$_8$ and R$_9$ are each independently selected from R$^a$, —Si—(R")$_3$ or —R'—Si—(R")$_3$, and at least one of R$_8$ and R$_9$ contains Si;
- R$^a$ and R" are each independently selected from H, C$_{1-12}$ alkyl, C$_{2-12}$ alkenyl, C$_{6-10}$ cyclohydrocarbyl or C$_{6-26}$ aryl;
- R' is selected from C$_{1-12}$ alkylidene or C$_{2-12}$ alkenylene;
- R$_{10}$ is C—R$^b$, and R$^b$ is selected from H, F, substituted or unsubstituted C$_{1-6}$ alkyl, or substituted or unsubstituted C$_{2-6}$ alkenyl, and R$_{11}$, R$_{12}$, R$_{13}$ and R$_{14}$ are independently selected from substituted or unsubstituted C$_{1-6}$ alkyl, substituted or unsubstituted C$_{1-6}$ alkoxy, substituted or unsubstituted C$_{2-6}$ alkenyl or substituted or unsubstituted C$_{6-10}$ aromatic ring, wherein, the substituent is selected from halogen, C$_{1-6}$ alkyl or C$_{2-6}$ alkenyl; and wherein the at least one cyclic N-containing sulfonyl-compound further comprises at least one of the following compounds of Formula I-4, Formula I-6, and Formula I-7:

(I-4)
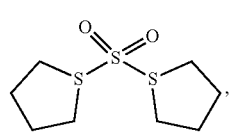, (I-6)
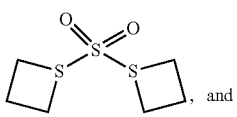, and

9. The electrochemical device according to claim 8, wherein the electrolyte further comprises a sulfur-oxygen double bond containing compound, wherein the sulfur-oxygen double bond containing compound comprises at least one of the following compounds of Formula II-A, II-B or II-C:

(II-A)
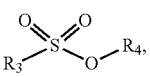

(II-B)

(II-C)
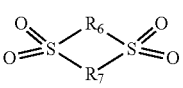

wherein,

- R$_3$ and R$_4$ are each independently selected from substituted or unsubstituted C$_{1-5}$ alkyl, substituted or unsubstituted C$_{2-10}$ alkenyl, substituted or unsubstituted C$_{6-10}$ aryl, or substituted or unsubstituted C$_{1-6}$ heterocyclic group; wherein, when substituted, they are substituted with one or more substituents selected from halogen, cyano, carboxy, or sulfate group;
- R$_5$ is selected from substituted or unsubstituted C$_{1-4}$ alkylidene, substituted or unsubstituted C$_{2-4}$ alkenylene, or substituted or unsubstituted C$_{1-6}$ chain alkane containing 1-5 heteroatoms selected from N, O, P and S, wherein, when substituted, they are substituted with one or more substituents selected from halogen, C$_{1-3}$ alkyl or C$_{2-4}$ alkenyl; and
- R$_6$ and R$_7$ are each independently selected from substituted or unsubstituted C$_{1-4}$ alkylidene, substituted or unsubstituted C$_{2-4}$ alkenylene, or substituted or unsubstituted C$_{1-6}$ chain alkane containing 105 heteroatoms selected from N, O, P and S, wherein, when substituted, they are substituted with one or more substituents selected from halogen, C$_{1-3}$ alkyl or C$_{2-4}$ alkenyl.

10. The electrochemical device according to claim 9, wherein the sulfur-oxygen double bond containing compound comprises at least on of the following compounds of Formula II-1 to Formula II-8:

(II-1)
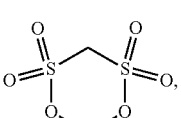

(II-2)
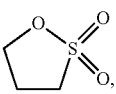,

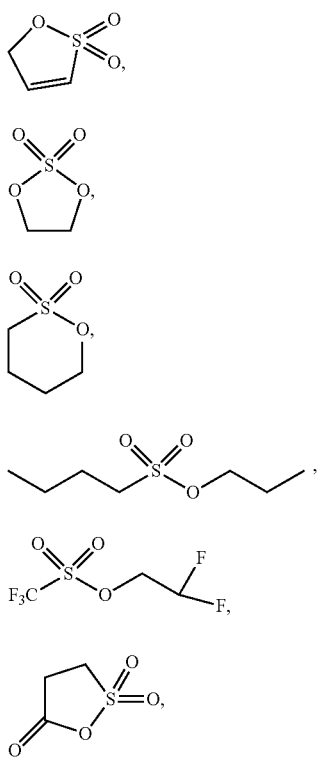

(II-3)
(II-4)
(II-5)
(II-6)
(II-7)
(II-8)

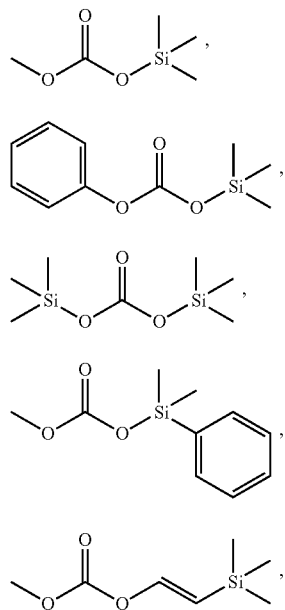

wherein based on the total weight of the electrolyte, the content of the sulfur-oxygen double bond containing compound is about 0.01 wt % to about 10 wt %.

11. The electrochemical device according to claim 8, wherein the silicon-containing carbonate comprises at least one of the following compounds of Formula III-1 to Formula III-5 and compounds of Formula IV-1 to Formula IV-3:

(III-1)
(III-2)
(III-3)
(III-4)
(III-5)

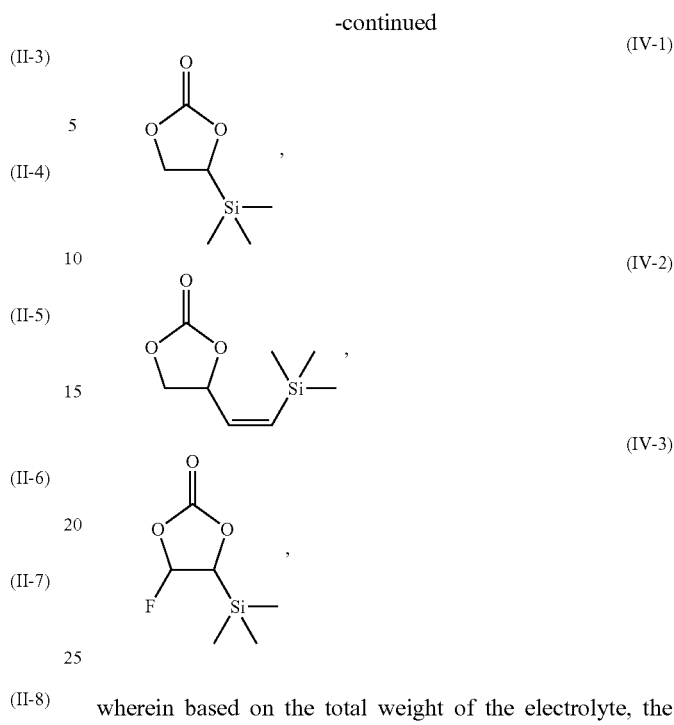

(IV-1)
(IV-2)
(IV-3)

wherein based on the total weight of the electrolyte, the content of the silicon-containing carbonate is about 0.1 wt % to about 20 wt %.

12. The electrochemical device according to claim 8, wherein based on the total weight of the electrolyte,
    the content of the at least one cyclic N-containing sulfonyl-compound is about 0.01 wt % to about 5 wt %,
    the content of the vinylene carbonate is about 0.001 wt % to about 4 wt %,
    the content of fluoroethylene carbonate is about 0.1 wt % to about 10 wt %,
    the content of lithium tetrafluoroborate is about 0.001 wt % to about 2 wt %, and
    the content of lithium difluorophosphate is about 0.001 wt % to about 2 wt %.

13. An electronic device, comprising:
    an electrochemical device comprising an electrolyte,
    wherein said electrolyte comprises at least one cyclic N-containing sulfonyl-compound of Formula I-1, Formula I-2, Formula I-3, or Formula I-5:

(I-1)
(I-2)
(I-3)

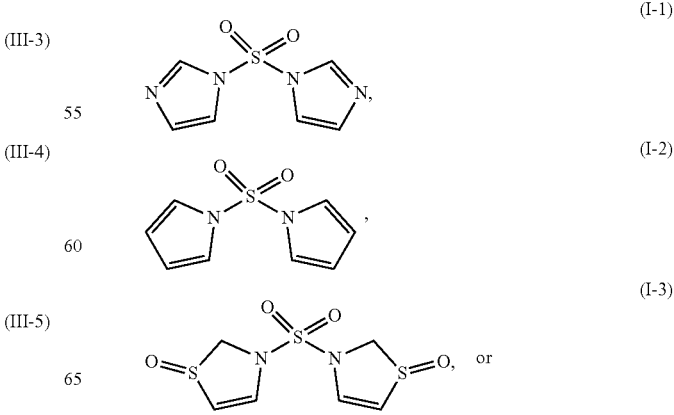

or

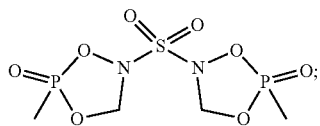 (I-5)

at least one of vinylene carbonate, fluoroethylene carbonate, lithium tetrafluoroborate, lithium difluoro(oxalate)borate or lithium difluorophosphate;

a silicon-containing carbonate selected from the following compounds of Formula III or Formula IV:

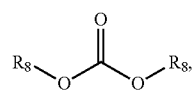 (III)

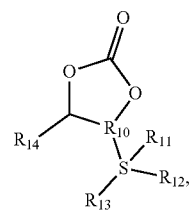 (IV)

wherein, $R_8$ and $R_9$ are each independently selected from $R^a$, —Si—$(R'')_3$ or —R'—Si—$(R'')_3$, and at least one of $R_8$ and $R_9$ contains Si;

$R^a$ and $R''$ are each independently selected from H, $C_{1-12}$ alkyl, $C_{2-12}$ alkenyl, $C_{6-10}$ cyclohydrocarbyl or $C_{6-26}$ aryl;

R' is selected from $C_{1-12}$ alkylidene or $C_{2-12}$ alkenylene;

$R_{10}$ is C—$R^b$, and $R^b$ is selected from H, F, substituted or unsubstituted $C_{1-6}$ alkyl, or substituted or unsubstituted $C_{2-6}$ alkenyl, and $R_{11}$, $R_{12}$, $R_{13}$ and $R_{14}$ are independently selected from substituted or unsubstituted $C_{1-6}$ alkyl, substituted or unsubstituted $C_{1-6}$ alkoxy, substituted or unsubstituted $C_{2-6}$ alkenyl or substituted or unsubstituted $C_{6-10}$ aromatic ring, wherein, the substituent is selected from halogen, $C_{1-6}$ alkyl or $C_{2-6}$ alkenyl; and wherein the at least one cyclic N-containing sulfonyl-compound further comprises at least one of the following compounds of Formula I-4, Formula I-6, and Formula I-7:

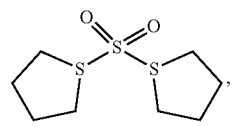 (I-4)

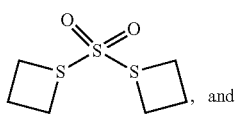 (I-6)

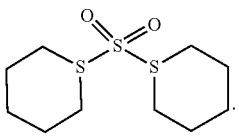 (I-7)

* * * * *